US00PP35860P2

(12) United States Plant Patent
Wilde

(10) Patent No.: US PP35,860 P2
(45) Date of Patent: Jun. 4, 2024

(54) ***SUTERA* PLANT NAMED 'KLESG22017'**

(50) Latin Name: *Sutera grandiflora*
Varietal Denomination: KLESG22017

(71) Applicant: KLEMM + SOHN GMBH & CO. KG, Stuttgart (DE)

(72) Inventor: Katinka Wilde, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 18/213,421

(22) Filed: Jun. 23, 2023

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./485
CPC ..... A01H 5/02; A01H 5/00; A01H 6/00
See application file for complete search history.

(56) References Cited

U.S. PATENT DOCUMENTS

PP23,835 P3 * 8/2013 Danziger ..... A01H 5/02 Plt./485
PP26,433 P3 * 2/2016 Klemm ..... A01H 6/00 Plt./485

OTHER PUBLICATIONS

GrowJoy Scopia Gulliver Blue Bacopa, retrieved on Sep. 28, 2023 at https://www.growjoy.com/store/pc/Scopia-Gulliver-Blue-Bacopa, 4 pp. (Year: 2023).*
Plant Lust Sutera Cordata Scopia Gulliver Blue PP23835 retrieved on Oct. 2, 2023 at https://plantlust.com/plants/39673/sutera-cordata-scopia-gulliver-blue/, 6 pp. (Year: 2023).*

* cited by examiner

*Primary Examiner* — June Hwu
(74) *Attorney, Agent, or Firm* — Weatherly IP Solutions, LLC; James M. Weatherly

(57) ABSTRACT

A new *Sutera* plant particularly distinguished by having a large purple-blue flowers and very good branching, is disclosed.

1 Drawing Sheet

Genus and species: *Sutera grandiflora.*
Variety denomination: 'KLESG22017'.

BACKGROUND OF THE NEW PLANT

The present invention comprises a new and distinct variety of *Sutera*, botanically known as *Sutera grandiflora*, and hereinafter referred to by the variety name 'KLESG22017'. 'KLESG22017' originated from a hand pollination between the proprietary female *Sutera* variety 'SG-2012-0347' (unpatented) and the commercial male *Sutera* variety Scopia® Gulliver Blue (U.S. Plant Pat. No. 23,835, 'Dancop37').

From May 2014 through July of 2014 controlled-crosses of the proprietary female *Sutera* line 'SG-2012-0347' male *Sutera* parental line, Scopia® Gulliver Blue were undertaken in a foil house in Stuttgart, German. Seed was collected and cleaned in the winter of 2014. In January 2015, seed were sown and plants were grown for evaluation in Stuttgart, Germany in a greenhouse under glass. A plant line was selected in May 2015 and subsequently named 'KLESG22017'. In May 2015, 'KLESG22017' was first vegetatively propagated in Stuttgart, Germany by asexual cuttings. 'KLESG22017' was found to reproduce true to type in successive generations of asexual propagation via asexual cuttings.

SUMMARY

The following are the most outstanding and distinguishing characteristics of this new variety when grown under normal horticultural practices in Stuttgart, Germany.

1. Large purple-blue flowers; and
2. Very good branching.

DESCRIPTION OF THE PHOTOGRAPH

This new *Sutera* plant is illustrated by the accompanying photograph which shows a close-up of the flowers. The photograph is of a 25-week-old plant grown in an outside environment in Stuttgart, Germany in August 2021. The colors shown are as true as can be reasonably obtained by conventional photographic procedures.

DESCRIPTION OF THE NEW VARIETY

The following detailed descriptions set forth the distinctive characteristics of 'KLESG22017'. The data which define these characteristics were collected from asexual reproductions carried out in Stuttgart, Germany. Data was collected on plants 7-weeks from potting grown in a foil house where no plant regulators were used in Stuttgart, Germany in April 2023. Color references are to the RHS Mini Colour Chart of The Royal Horticultural Society of London (R.H.S.), (2005).

Classification:
*Family.*—Scrophulariaceae.
*Botanical.*—*Sutera grandiflora.*
*Common.*—*Sutera.*
*Designation.*—'KLESG22017'.

Parentage:

*Female parent.*—Proprietary *Sutera* line 'SG-2012-0347' (unpatented).

*Male parent.*—*Sutera* line Scopia® Gulliver Blue (U.S. Plant Pat. No. 23,835, 'Damcop37').

Plant:

*Habit.*—Trailing and flat.

*Height.*—7.5 cm.

*Spread.*—30.0 cm.

*Life cycle.*—Blooms from spring until September.

*Form.*—Trailing and round.

*Time to produce a rooted cutting.*—3 weeks.

*Time to bloom from propagation.*—Finished product could be observed after 5-6 weeks after potting.

*Lastingness of inflorescence on the plant.*—About 7 days.

*Rooting habit.*—Fine, fibrous roots.

*Root color.*—White (RHS 155C) to cream white, getting brown if too wet.

Stems:

*Number of stems per plant.*—6.

*Length.*—About 16.5 cm.

*Diameter.*—0.3 cm.

*Internode length.*—3.0 cm.

*Color.*—RHS 144B.

*Texture.*—Pubescence.

*Anthocyanin.*—Absent.

Leaves:

*Arrangement.*—Single, opposite.

*Type.*—Simple.

*Number of leaves per branch.*—5 pairs, without side shoots and their leaves.

*Shape.*—Ovate.

*Variegation.*—Absent.

*Apex.*—Acuminate.

*Base.*—Cordate.

*Margin.*—Serrate.

*Length.*—Between 1.0 cm to 3.5 cm.

*Width.*—Between 0.6 cm and 3.0 cm.

*Color.*—Immature leaf: Upper surface: RHS 147A. Lower surface: RHS 147B. Mature leaf: Upper surface: RHS 147A. Lower surface: RHS 147B.

*Texture.*—Both upper and lower surfaces: Pubescence.

*Venation type.*—Pinnate.

*Venation color.*—Upper surface: RHS 147A. Lower surface: RHS 147B.

*Petiole.*—Length: immature leaf: 0.2 cm mature leaf: 0.4 cm. Diameter: 0.2 cm. Texture: Pubescence. Color: RHS 146C.

Inflorescence:

*Blooming habit.*—Freely flowering.

*Quantity of inflorescence per stem.*—6.

*Type of inflorescence.*—Single, salverform flowers.

*Persistent or self-cleaning flower.*—Self-cleaning flower.

*Fragrance.*—Present but only foliage not flowers.

*Natural flowering season.*—Spring until September.

Peduncle:

*Length.*—1.2 cm.

*Diameter.*—0.2 cm.

*Color.*—RHS 146B.

*Texture.*—Pubescence.

*Strength.*—Thin.

Bud:

*Shape.*—Tubular.

*Diameter.*—0.6 cm.

*Length.*—1.1 cm.

*Color (at tight bud).*—RHS 145C and later RHS 86C.

Corolla (flower):

*Type and shape.*—Single-type, nearly round, lower part tube and funnel shaped formed by 5 fused petals, upper part is salver shaped formed by the partly free petal lobes.

*Corolla, horizontal diameter.*—2.7 cm.

*Corolla, total length.*—1.5 cm. Color of throat: Inner surface: RHS 13A. Outer surface: RHS 145D. Tube/funnel:

*Length.*—1.0 cm.

*Diameter.*—0.3 cm.

*Texture of funnel.*—

*Inner surface.*—Leathery.

*Outer surface.*—Leathery.

Petal (lobes):

*Length.*—1.2 cm.

*Width.*—0.9 cm.

*Apex.*—Rounded tips.

*Base.*—Fused to a tube.

*Margin.*—Entire.

*Color.*—Inner surface: RHS 86D, purple violet in juvenile phase at the base of the petal lobes, with a small section of pink (RHS 80B). Young flowers a purple violet ring at the base, fading to only violet (RHS 86D) with maturity. Outer surface: RHS 86D fading to white in direction to the tunnel.

*Texture.*—Upper surface: Leathery. Lower surface: Leathery.

Calyx:

*Arrangement and appearance.*—Whorl of 5 sepals surrounding the base of the flower tube, sepals are fused at the base.

*Sepals.*—Color: Upper surface: RHS 137B. Lower surface: RHS 137B. Length: 1.0 cm. Width: 0.1 cm. Shape: 5 sepals fused at the base. Apex: Acuminate. Base: Fused. Margin: Entire. Texture: Upper surface: Pubescence. Lower surface: Pubescence.

Reproductive organs:

*Stamens.*—Quantity: 4. Filament: Color: RHS 145C. Length: 0.6 cm. Diameter: 0.1 cm. Anther color: RHS 14B. Pollen amount: Abundant. Pollen color: RHS 13A.

*Pistil.*—Quantity per flower: 1. Length: 0.9 cm. Stigma color: RHS 145A. Style color: RHS 145A. Style length: 0.8 cm. Ovary color: RHS 145B.

*Fruit and seed set.*—None observed.

*Disease and pest/insect resistance.*—None observed.

COMPARISON WITH PARENTAL LINE AND KNOWN VARIETY

'KLESG22017' is a distinct variety of *Sutera* having a blue flower color; 'KLESG22017' is distinguished from its female and male parents as described in Table 1:

TABLE 1

| Comparison with Parental Line | | | |
|---|---|---|---|
| Trait | Variety 'KLESG22017' | Female parent 'SG-2012-0347' | Male parent Scopia ® Gulliver Blue |
| Branching | Very good branching | Very good branching | Less branching |
| Flower color | Purple-blue | Pink | Blue |
| Flower size | Large | Medium | Large |

'KLESG22017' is most similar to the *Sutera* plant named 'KLESG12346' (U.S. Plant Pat. No. 26,433). Differences between the two varieties are described in Table 2:

TABLE 2

| Comparison with Similar Variety | | |
|---|---|---|
| Trait | Variety 'KLESG22017' | Similar variety 'KLESG12346' |
| Branching | Very good branching | Good branching |
| Internode length | Compact/short | Long/stretchy |
| Summer performance | Very good | Low, flower break more often |

I claim:

1. A new and distinct cultivar of *Sutera* Plant Named 'KLESG22017' as described and illustrated herein.

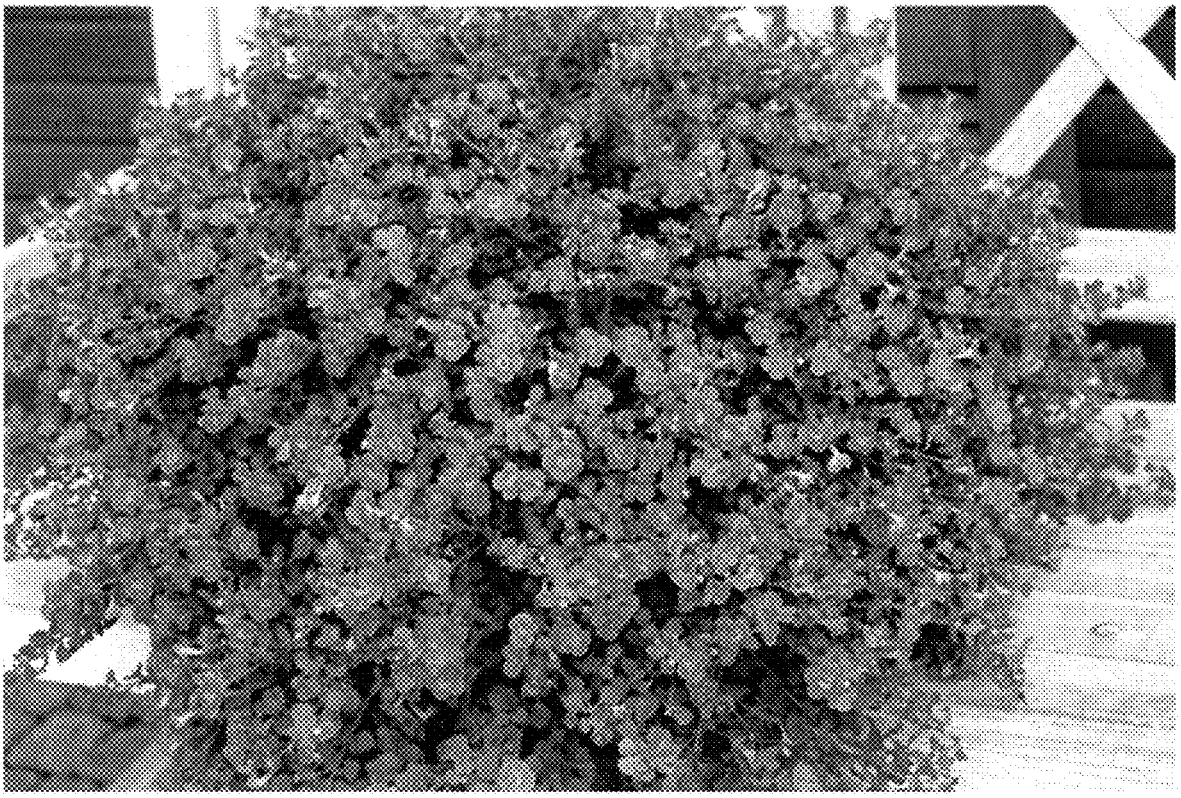

* * * * *